United States Patent [19]
Patterson

[11] 3,963,557
[45] June 15, 1976

[54] ARTICLE TRANSFERRING APPARATUS

[75] Inventor: Richard A. Patterson, Woodbury, Minn.

[73] Assignee: Minnesota Mining and Manufacturing Company, St. Paul, Minn.

[22] Filed: Apr. 28, 1975

[21] Appl. No.: 571,907

Related U.S. Application Data

[63] Continuation-in-part of Ser. No. 473,327, May 28, 1974, abandoned.

[52] U.S. Cl. .............................. 156/519; 156/568
[51] Int. Cl.² ..................... B32B 31/00; B65C 9/00
[58] Field of Search ........... 156/519, 521, 568, 570, 156/571

[56] References Cited
UNITED STATES PATENTS

| | | | |
|---|---|---|---|
| 2,543,220 | 2/1951 | Ardell | 156/521 |
| 2,990,081 | 6/1961 | De Neui et al. | 156/519 |
| 3,087,355 | 4/1963 | Bassereau | 74/793 |
| 3,418,858 | 12/1968 | Minnich | 74/68 |
| 3,591,168 | 7/1971 | Zodrow | 156/568 |
| 3,736,213 | 5/1973 | Jorss et al. | 156/576 |
| 3,905,859 | 9/1975 | Patterson | 156/521 |
| 3,919,040 | 11/1975 | Zodrow | 156/571 |

*Primary Examiner*—Douglas J. Drummond
*Attorney, Agent, or Firm*—Alexander, Sell, Steldt & DeLaHunt

[57] ABSTRACT

A vacuum applicating apparatus for dispensing and applying measured lengths of tape on a moving substrate. The apparatus has a plurality of rotating applicating segments which are driven by a driving wheel. The segments can be disposed so that tape is fed onto the segments from a continuous supply of tape at a slow speed; the tape is then severed into measured lengths and the lengths are applied in spaced relationship onto a faster moving substrate.

9 Claims, 6 Drawing Figures

3,963,557

ARTICLE TRANSFERRING APPARATUS

RELATED APPLICATIONS

This application is a continuation-in-part of application Ser. No. 473,327 filed May 28, 1974 now abandoned.

BACKGROUND OF THE INVENTION

1. Field of The Invention

This invention pertains to a vacuum operated tape applicating apparatus, and in one aspect this invention relates to devices suitable for receiving continuously supplied articles to a moving receiver in a predetermined spaced relationship. The articles may be tape pieces fed from a continuous roll, labels or other articles to be handled and spaced.

2. Prior Art

The prior art discloses vacuum wheel applicators for pressure-sensitive adhesive tapes wherein the tape is applied to the periphery of a wheel and the tape is severed into lengths which are applied to the wheel to a moving substrate. See for example the U.S. Pat. No. 2,990,081, de Neui et al issued June 27, 1961 and copending de Neui patent application in the United States, Ser. No. 288,757 filed Sept. 13, 1972.

The prior art devices require that the tape be applied to the wheel at a speed different than the peripheral speed of the wheel and the speed of the moving substrate. Spacing the strips on the moving substrate requires greater variations in the relative speed of the applicating wheel and the feeding of the tape. The speed difference between the tape and the periphery of the wheel may result in abrasion of the tape and/or wheel, and adhesive backsize buildup on the wheel as a result of the relative movement.

Prior to this invention the tape was fed in increments or the tape was moved continuously onto a moving vacuum wheel but at a different speed, thus resulting in relative movement between the tape and the vacuum wheel which with some tape compositions, results in abrasion of the tape backing, producing an objectionable dust. One example of where such a problem existed was the manufacture of disposable diapers where a tape composition initially produced an objectionable abrasion. The diapers are normally produced as a continuous sheet and tape tabs are applied at spaced intervals followed by cutting the sheet into individual diapers.

The applicating apparatus of this invention provides a solution to the problems of the prior art vacuum wheel applicators and allows the application of measured lengths of tape withdrawn continuously from a roll of tape, placed onto the applicator, cut to the length and placed onto a moving substrate without relative movement between the tape and the applicator. Indeed, the apparatus of this invention is an improvement in that the tape is moved at one speed and the cut strips are applied at a greater speed and in a spaced relationship to the substrate with a continuous tape drive and without relative movement between the tape and the surface of the applicating segments.

SUMMARY OF THE INVENTION

The apparatus of this invention comprises a driving wheel rotatably mounted on a first fixed axis supported by a frame and having a plurality of radially extending cam surfaces thereon. A plurality of article supporting segments, having article supporting surfaces, are rotatably mounted on a second fixed axis supported by the frame. The second axis is parallel to and spaced from the rotational axis of the driving wheel. Cam followers are attached to the article supporting segments and are engageable with the cam surfaces of the driving wheel so that rotation of the driving wheel will move the cam followers and thereby the segments about the second axis.

Drive means apply a continuous supply of articles, or a strip of tape having a normally tacky pressure-sensitive adhesive disposed on one side thereof, to the supporting surfaces of the segments with the adhesive side exposed. There are means for applying a vacuum to the article supporting segments to hold e.g. the tape in contact with the supporting surface of the segments to grasp or hold the tape until the tape is applied to a substrate. Cutting means sever the tape to predetermined lengths which lengths of tape will be held on said segments by the vacuum.

Where the first and second axis are offset, the cam followers, moved by the rotation of the driving wheel, will be driven at a speed which changes continuously as the segments rotate whereby the segments can transfer the articles to the receiver, e.g. the lengths of tape to a substrate, at a speed different from the speed at which the article is supplied to the segment. The speed of the segment at the transfer area will be matched to the speed of the receiver or substrate and the speed at the receiving area to supply articles to the segments will be matched most preferably.

BRIEF DESCRIPTION OF THE DRAWING

A further understanding may be had by referring to the accompanying drawing in which.

DETAILED DESCRIPTION OF THE PREFERRED EMBODIMENTS

Figure 1:
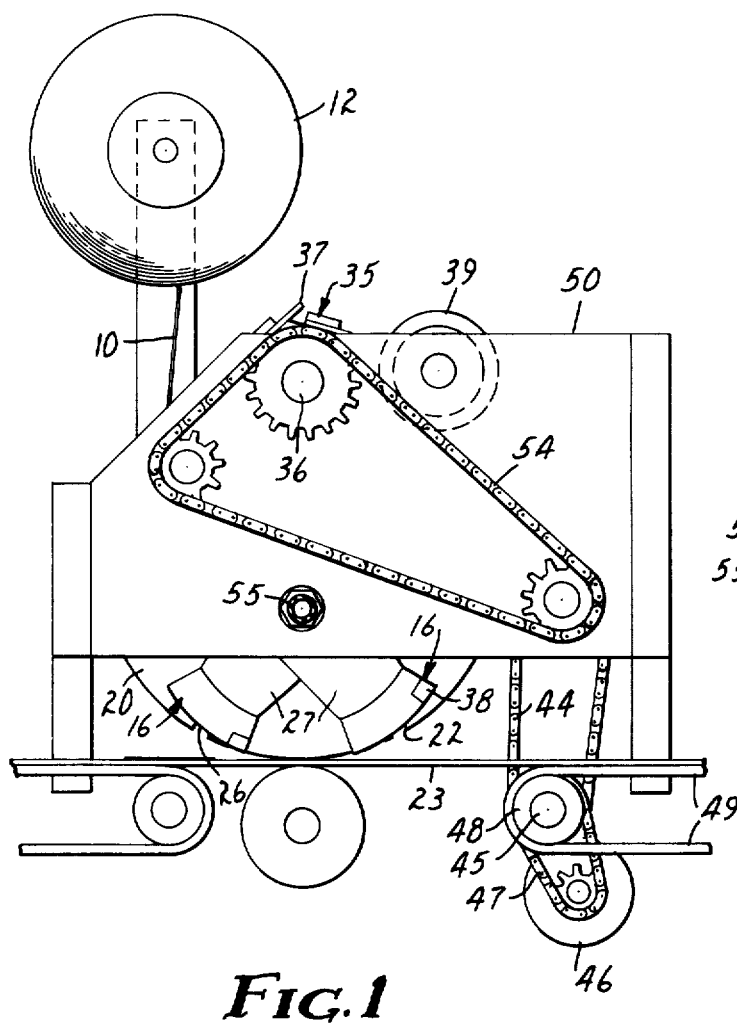
FIG. 1 is a front elevational view of a tape applicator constructed in accordance with this invention.
Figure 2:
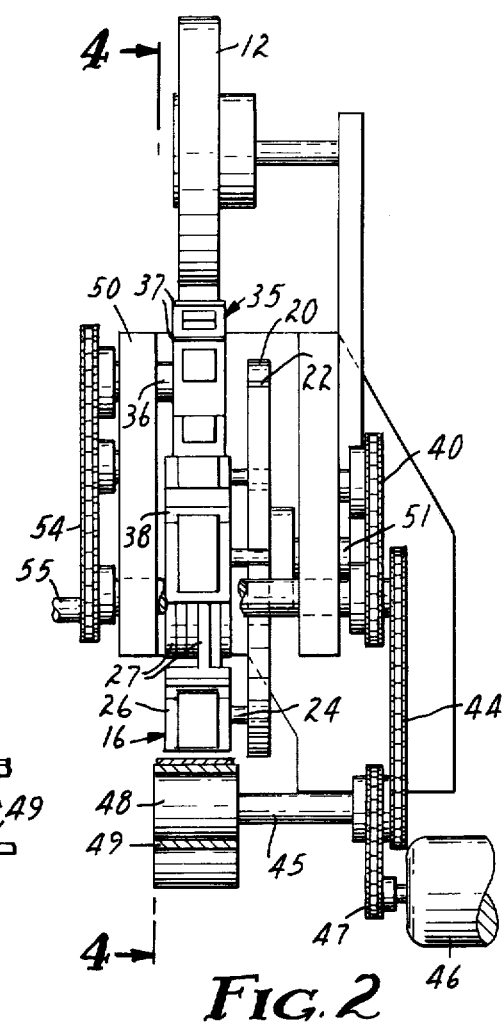
FIG. 2 is an end elevational view of the applicator of FIG. 1 with parts removed to show parts in back.
Figure 4:
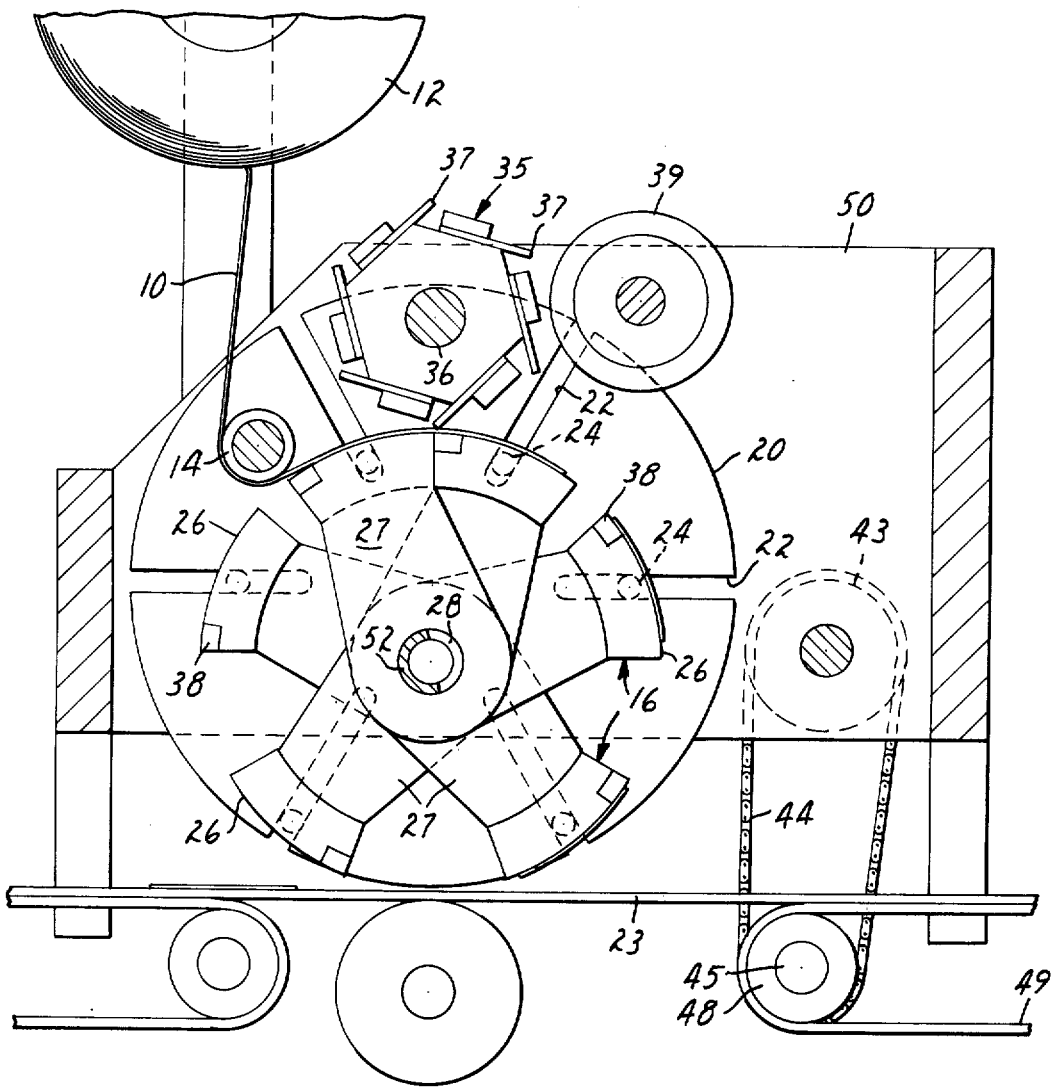
FIG. 4 is a vertical sectional view taken approximately along the line 4—4 of FIG. 2.

Referring to the drawing and initially to FIGS. 1 and 4, a strip of tape 10 having a pressure-sensitive adhesive disposed on one side of a flexible backing is fed from a convolutely wound supply roll 12 passing under a roller 14 onto article supporting segments 16 in a continuous fashion. The tape is placed on the segments at the tape receiving position of the segments with the adhesive exposed and the back or nonadhesive side being held against the article supporting surface of the applicating segments 16 by means of a vacuum applied through perforations in the surface. After the tape 10 is fed onto the applicating segment 16, it passes by a cutting means which severs the tape into measured lengths.

Each applicating segment 16 carrying the cut length of tape will be driven about an axis by cam follower 24 engaging a cam surface 22 on driving wheel 20. The segments are rotated to a transfer position where the adhesive on the length of tape will contact a moving substrate 23 and the adhesive will transfer the tape from the segment to the substrate. The empty segment will continue to rotate back into position to receive an additional length of tape.

More specifically, the tape 10 is unwound from a convolutely wound supply roll 12, comprising a substantial length of tape which can be wrapped about a core and passes under a knurled drive roller 14, the adhesive side of the tape making contact on the roller. The tape can be advanced continuously by driving the roller 14 which pulls tape off the roll and directs it onto the segments at a linear speed matching the surface speed of the segments. As the tape is fed onto the applicating segments, holding means hold the tape on the periphery 26 of the applicating segments 16. As illustrated, the tape is held by means of a vacuum, i.e. subatmospheric pressure, being developed within a plurality of tiny openings 34 formed in the supporting surface of each segment. The vacuum is supplied by a manifold 28 which is connected to a chamber 30 in the applicating segment 16 by a bore 32. The chamber 30 communicates with face 26 by means of the plurality of openings or apertures 34. The vacuum is applied to chamber 30 during the rotative movement of the segments between the point at which the tape 10 contacts the applicating segment and the position where the tape is applied to the substrate at which position the vacuum to the chamber is preferably cut off.

The cutting means can comprise a rotary shear and anvil. As illustrated, rotary shear 35 is mounted on shaft 36 and has a plurality of flexible blades 37 extending outwardly therefrom suitable for severing the tape 10 into measured lengths. The blades 37 cooperate with small hard steel anvils 38 located at one end of each surface of the applicating segments 16. The tape 10 can be severed by applying a substantial compressive force with the shear blade 37 against the anvil 38, a sharp cutting edge not being required to cut the tape. A wheel 39 is supported on a support frame 50 to be engaged by the edges of the blades to oil the edges and restrict adhesive from transferring thereto during the cutting.

Figure 3:
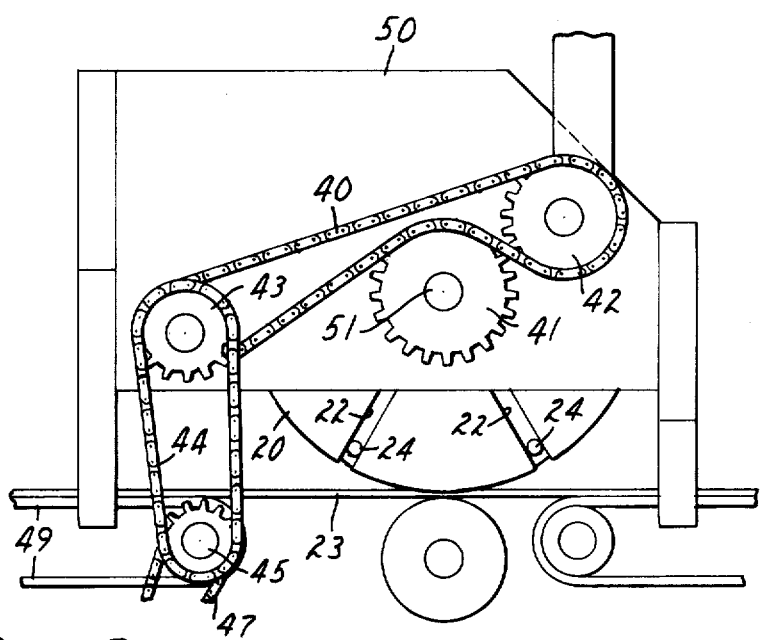
FIG. 3 is a rear elevational view of the applicator of FIG. 1.

The driving wheel 20 has a plurality of cam surfaces shown as a plurality of radially extending cam slots 22 and is driven at a constant speed by a belt or chain 40, sprockets 41, 42, and 43 and chain 44 from a jack shaft 45 driven from a motor 46 by a chain 47. The jack shaft 45 also drives a roller 48 to drive a conveyor 49 for moving the article receiving substrate 23. As the driving wheel 20 turns about a first axis, defined by a stub shaft 51 (FIG. 3) mounted on the frame 50, the cam followers 24 attached to the applicating segments 16 will be moved rotating the applicating segments about a second axis defined by shaft 52. A drive chain 54 drives the rotary shear 34 in timed relationship to the segments 16 and feed roller 14. As shown the axis of rotation for the segments 16 is located between the substrate 23 to which the cut length of tape is to be applied and the axis of rotation of the driving wheel 20. Thus, as the cam followers 24 move in cam slots 22 during rotation of the driving wheel 20, the cam followers move from a position near the center of the driving wheel to a position near the periphery of the driving wheel. The resulting increase in speed of the segments 16 causes a separation between adjacent applicating segments as they approach the substrate and the tape will be applied at the applying position at spaced intervals on the substrate. The shape of the slots 22 determine the pattern of movement of the segments but the cam surfaces must be generally radial. Also, the measured lengths of tape are applied to a substrate moving at a higher rate of speed than the rate at which the tape is fed onto the applicating segments 16.

Because the motion of the applicating segments 16 is slow when the tape 10 is applied, the apparatus of this invention permits easy feeding and cutting of the tape without the use of a reciprocating roller to match the tape feed and shear at the point of cutting. In addition, the apparatus of this invention allows the tape feed speed to be matched accurately with the applicating segment eliminating the sliding action of tape and consequently a buildup of abraded tape and substrate material on the segments as a result of relative motion therebetween. The speed of the segment is matched with the speed of the receiver or substrate at the transfer area to transfer the tape smoothly.

Figures 5, 6:
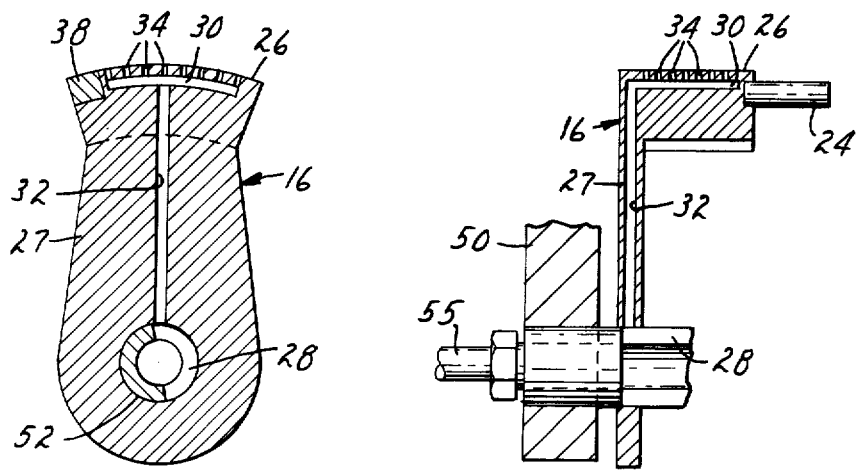
FIG. 5 is a longitudinal sectional view of one applicating segment.
FIG. 6 is a transverse sectional view of an applicating segment.

The structure of applicating segments 16 is shown in greater detail in FIGS. 5 and 6. The plurality of openings 34 in the surface 26 of the applicating segment 16 communicate with a vacuum chamber 30 within the head of the segment. The vacuum chamber 30 is connected by means of a bore 32, through segment leg 27, to the manifold 28 in the shaft 52. As shown, the manifold 28 is designed to provide a reduced pressure to the chamber 30 throughout approximately half of the application cycle. The vacuum is applied to the supporting surface 26 from near the point where the tape is received by the applicating segments 16 to the point at which the tape is applied to the substrate. Near the point where the severed lengths of tape are applied to the moving substrate, the vacuum is cut off to restrict the amount of air which must be pumped and the noise of the machine. Thus, the bore 32 will not be in fluid communication with the manifold 28 as the segment moves from the applicating or transfer position around to the point at which tape is again received by the applicating surface 26. The vacuum of subatmospheric pressure in the manifold 28 is provided by suitable pumps or means not shown and a conduit 55 connected to the fixed shaft 52.

Holding means other than the vacuum shown and described can be used. Some examples include electrostatic forces, magnetic forces or mechanical means such as gripping members or recesses and fixed guide members all of which are suitable for holding various articles on the supporting surface of each segment between the receiving area and the transfer area.

Although the invention has been described with respect to one specific embodiment, it is to be understood that various modifications and alterations will become apparent to those skilled in the art, and it is to be understood that this invention is not limited to the illustrative embodiment described hereinbefore.

I claim:

1. An apparatus suitable for receiving articles fed thereto continuously at a first feed rate and transferring said articles to a receiver at a different rate in different spacial relationship, said apparatus comprising:
   a frame;
   a driving wheel rotatably mounted on said frame on a first axis and having a plurality of generally radially extending cam surfaces;
   means for rotating said driving wheel;
   a plurality of supporting segments, each having an article supporting surface, rotatably mounted on arms extending radially outward from a second axis in parallel, spaced, fixed relationship to said first axis and supported by said frame;

cam followers attached to said segments and engaged with said cam surfaces on said driving wheel for imparting the rotational force of said driving wheel to said segments to rotate said segments about said second fixed axis;

drive means for feeding a continuous supply of articles to the supporting surface of said segments at an article receiving area;

holding means for holding individual articles in contact with a said supporting surface of each said segment between said receiving area and a transfer area spaced therefrom about the path of rotation of said supporting surfaces about said second axis whereby, upon rotation of said driving wheel, said supporting surfaces are driven about said second axis past said receiving area to receive an article and then to said transfer area to transfer the articles to a receiver in a different spacial relationship.

2. An apparatus according to claim 1 wherein said cam surfaces are radial slots in said driving wheel and said cam followers are pins extending from each segment into said slots and said first and second axis cooperate so that adjacent supporting segments have their surfaces together when the segments are at the receiving area and spaced at the transfer area, said transfer area being spaced in a direction from said first axis a distance greater than said second axis.

3. A tape applying apparatus suitable for dispensing measured lengths of tape on a moving substrate comprising:

a frame;

a driving wheel rotatably mounted on a first axis relative to said frame and having a plurality of generally radial cam surfaces;

means for rotating said driving wheel;

a plurality of applicating segments, having an applicating surface, rotatably mounted on arms extending radially outward from a second axis in parallel, spaced, fixed relationship to said first axis and supported by said frame;

cam followers attached to said segments and engaged with said cam surfaces on said driving wheel for imparting the rotational force on said driving wheel to said segments to rotate said segments about said second fixed axis;

drive means for feeding a continuous strip of tape to the applicating surface of said segments with the adhesive side exposed;

holding means for holding said tape in contact with said applicating surface of said segment;

cutting means for severing said tape into predetermined lengths of tape;

whereby as said cam followers are moved by the rotation of said driving wheel, said applicating segments are driven about said second axis from a tape receiving position to a tape applying position so that said lengths of tape are carried by said segments into contact with said moving substrate thereby applying the lengths of tape to said substrate.

4. The apparatus of claim 3 wherein said holding means comprises a plurality of openings in said applicating surface and a vacuum source in fluid communication with said openings applying a vacuum to said openings throughout that portion of the applicating cycle that said tape is in contact with said applicating surface.

5. The apparatus of claim 3 wherein said cutting means comprises a cutting head having a plurality of cutting blades which will cooperate with a hardened steel anvil attached to each of said segments to sever lengths of tape with said segments at said tape receiving position.

6. The apparatus of claim 3 wherein said second axis is positioned between the path of said substrate and said first axis and the tape is fed onto said segment at a position closer to said first axis than said substrate whereby said applicating segments are driven at a variable speed so the tape is fed onto said segment at a low speed and said measured lengths of tape are applied to said substrate at a higher rate of speed than said tape was applied to said segment thereby applying said lengths of tape in a spaced relationship on the substrate at a speed matched to the rate of the substrate.

7. The apparatus of claim 3 wherein said cam surfaces are radially extending cam slots and said cam followers are pins mounted on said segments extending axially into engagement with said slots.

8. The apparatus of claim 3 wherein said cam surfaces are radial slots in said wheel and said first and second axis cooperate so that adjoining applicating segments are together when the segments are at said tape receiving position adjacent said cutting means.

9. A material carrying and transferring apparatus for transferring material contacted therewith to a second moving receptor comprising:

a frame;

a driving wheel rotatably mounted on a first axis relative to said frame and having a plurality of generally radially extending cam tracks;

means for rotating said driving wheel;

a plurality of material transferring segments, having a material supporting surface, rotatably mounted on arms extending radially outward from a second axis in parallel, spaced, fixed relationship to said first axis and supported by said frame;

cam followers attached to said segments and engaging said cam tracks on said driving wheel for imparting the rotational force of said driving wheel to said segments to rotate said segments about said second axis;

drive means for feeding a continuous supply of material to the supporting surface of said segments when said segments are positioned at a material receiving position with respect to the path of movement thereof to place material in contact with each contacting surface of each segment, and receptor means spaced about the path of movement of said segments for receiving material transferred thereto by said contacting surfaces.

* * * * *

UNITED STATES PATENT AND TRADEMARK OFFICE
CERTIFICATE OF CORRECTION

PATENT NO. : 3,963,557
DATED : June 15, 1976
INVENTOR(S) : Richard A. Patterson

It is certified that error appears in the above-identified patent and that said Letters Patent are hereby corrected as shown below:

Column 1, line 13, change "receiving" to -- transferring --.

Column 1, line 3, change "difference" to -- differential --.

Signed and Sealed this

Ninth Day of November 1976

[SEAL]

Attest:

RUTH C. MASON
*Attesting Officer*

C. MARSHALL DANN
*Commissioner of Patents and Trademarks*